(12) United States Patent
Snowden et al.

(10) Patent No.: US 12,210,016 B2
(45) Date of Patent: Jan. 28, 2025

(54) DIAGNOSTIC TEST DEVICE WITH IMPROVED USE AND VISUAL DETECTION OF AN ANALOG TEST RESULT

(71) Applicant: Church & Dwight Co., Inc., Princeton, NJ (US)

(72) Inventors: Timothy Snowden, Howell, NJ (US); Sujata Sundara Rajan, Belle Mead, NJ (US); Christopher King, Hampton, NJ (US); Jonathan Andrew Wharton, Ewing, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 305 days.

(21) Appl. No.: 17/358,095

(22) Filed: Jun. 25, 2021

(65) Prior Publication Data

US 2021/0405045 A1 Dec. 30, 2021

Related U.S. Application Data

(60) Provisional application No. 63/044,654, filed on Jun. 26, 2020.

(51) Int. Cl.
*G01N 33/543* (2006.01)
*G01N 33/74* (2006.01)
*G01N 33/76* (2006.01)

(52) U.S. Cl.
CPC ..... *G01N 33/54388* (2021.08); *G01N 33/743* (2013.01); *G01N 33/76* (2013.01); *G01N 2333/59* (2013.01)

(58) Field of Classification Search
CPC .......... G01N 33/54388; G01N 33/743; G01N 33/76; G01N 2333/59; G01N 2201/062; G01N 2201/0694; G01N 2201/08; G01N 21/8483
See application file for complete search history.

(56) References Cited

U.S. PATENT DOCUMENTS

| | | |
|---|---|---|
| 5,572,370 A | 11/1996 | Cho |
| 5,580,794 A | 12/1996 | Allen et al. |
| 5,739,041 A | 4/1998 | Nazareth et al. |
| 5,837,546 A | 11/1998 | Allen et al. |
| 5,846,835 A | 12/1998 | Sisbarro et al. |
| 6,046,057 A | 4/2000 | Nazareth et al. |
| 6,235,241 B1 | 5/2001 | Catt et al. |
| 6,277,650 B1 | 8/2001 | Nazareth et al. |
| 6,319,676 B1 | 11/2001 | Nazareth et al. |
| 6,485,982 B1 | 11/2002 | Charlton |

(Continued)

FOREIGN PATENT DOCUMENTS

WO 2019025609 2/2019

*Primary Examiner* — Dennis White
(74) *Attorney, Agent, or Firm* — Church & Dwight Co., Inc.

(57) ABSTRACT

The present disclosure relates to diagnostic test devices that provide improved communication to a user of one or both of proper functioning of the test device and an analog test result that is provided by the test device. The diagnostic test devices particularly can include one or more sensors effective to indicate application of a sufficient volume of a test fluid and/or can include one or more light sources positioned to illuminate an analog test result for improved visibility and understanding of the analog test result.

23 Claims, 5 Drawing Sheets

(56) References Cited

U.S. PATENT DOCUMENTS

| | | |
|---|---|---|
| 6,660,141 B1 | 12/2003 | Minter et al. |
| 6,767,714 B2 | 7/2004 | Nazareth et al. |
| 6,951,631 B1 | 10/2005 | Catt et al. |
| 7,045,342 B2 | 5/2006 | Nazareth et al. |
| 7,214,542 B2 | 5/2007 | Hutchinson et al. |
| 7,220,597 B2 | 5/2007 | Zin et al. |
| 7,315,378 B2 | 1/2008 | Phelan et al. |
| 7,317,532 B2 | 1/2008 | Sharrock et al. |
| 7,369,331 B2 | 5/2008 | Sachdev et al. |
| 7,499,170 B2 | 3/2009 | Sasaki et al. |
| 7,763,454 B2 | 7/2010 | Nazareth et al. |
| 7,776,618 B2 | 8/2010 | Nazareth et al. |
| 7,879,624 B2 | 2/2011 | Sharrock |
| 8,211,711 B2 | 7/2012 | Nazareth et al. |
| 8,268,636 B2 | 9/2012 | Nazareth et al. |
| 8,722,395 B2 | 5/2014 | Nazareth et al. |
| 9,151,749 B2 | 10/2015 | Raj et al. |
| 9,689,821 B2 | 6/2017 | Barnard et al. |
| 9,915,617 B2 | 3/2018 | Wu et al. |
| 9,973,399 B2 | 5/2018 | Yang et al. |
| 10,070,847 B2 | 9/2018 | Hung et al. |
| 10,168,322 B2 | 1/2019 | Nazareth et al. |
| 10,328,427 B2 | 6/2019 | Lehane et al. |
| 2002/0042082 A1 | 4/2002 | Nazareth et al. |
| 2003/0044317 A1* | 3/2003 | Catt ............... G01N 21/8483 422/402 |
| 2004/0082878 A1* | 4/2004 | Baldwin ............ B01L 3/5029 422/50 |
| 2004/0152208 A1* | 8/2004 | Hutchinson ......... G01N 33/523 702/19 |
| 2004/0171174 A1 | 9/2004 | Nazareth et al. |
| 2006/0194342 A1 | 8/2006 | Bond et al. |
| 2008/0213920 A1 | 9/2008 | Nazareth et al. |
| 2010/0051350 A1 | 3/2010 | McClain et al. |
| 2010/0239460 A1 | 9/2010 | Nazareth et al. |
| 2010/0240149 A1 | 9/2010 | Nazareth et al. |
| 2010/0261293 A1 | 10/2010 | Nazareth et al. |
| 2010/0267166 A1 | 10/2010 | Nazareth et al. |
| 2011/0201122 A1 | 8/2011 | Nazareth et al. |
| 2012/0083044 A1 | 4/2012 | Sturman et al. |
| 2014/0296667 A9 | 10/2014 | Dahl et al. |
| 2015/0226752 A1 | 8/2015 | Nazareth et al. |
| 2016/0022225 A1 | 1/2016 | Palmer et al. |
| 2016/0027283 A1 | 1/2016 | Palmer et al. |
| 2018/0259500 A1 | 9/2018 | Sturman et al. |
| 2018/0340932 A1 | 11/2018 | Emeric et al. |

* cited by examiner

DIAGNOSTIC TEST DEVICE WITH IMPROVED USE AND VISUAL DETECTION OF AN ANALOG TEST RESULT

CROSS-REFERENCE TO RELATED APPLICATIONS

The present application claims priority to U.S. Provisional Patent Application No. 63/044,654, filed Jun. 26, 2020, the disclosure of which is incorporated herein by reference in its entirety.

FIELD OF THE DISCLOSURE

The present disclosure relates to diagnostic test devices that provide user connectivity. More particularly, the test devices include elements that provide for specific feedback to the user, such as through visual means.

BACKGROUND

Many types of ligand-receptor assays have been used to detect the presence of various substances in body fluids, such as urine, saliva, or blood. Some commercially available assays are designed to make a quantitative determination, but in many circumstances all that is required is a qualitative positive/negative indication. Examples of such qualitative assays include blood typing, pregnancy testing, and many types of urinalysis.

U.S. Pat. No. 6,485,982, which is incorporated herein by reference in its entirety, describes a diagnostic test cell or device formed of an elongate outer casing which houses an interior permeable material (such as glass fiber) capable of transporting an aqueous solution by capillary action, wicking, or simple wetting. The casing defines a sample inlet, and interior regions, which are designated as a test volume and a reservoir volume. The reservoir volume is disposed in a section of the test cell spaced apart from the inlet and is filled with sorbent material. The reservoir acts to receive a fluid sample transported along a flow path defined by the permeable material and extending from the inlet and through the test volume. In the test volume is a test site comprising a first protein having a binding site specific to a first epitope of the ligand immobilized in fluid communication with the flow path (e.g., bound to the permeable material or to latex particles entrapped in or bonded to the permeable material). A window, such as a hole or transparent section of the casing, permits observations of the test site through the casing wall. The use of the test cell requires a conjugate comprising a second protein bound to colored particles, such as a metal sol or colloid, preferably gold. The conjugate can take two distinct forms, depending on whether the assay is designed to exploit the "sandwich" or "competitive" technique.

U.S. Pat. No. 7,045,342, which is incorporated herein by reference in its entirety, describes a diagnostic test device including a biphasic chromatographic medium. The biphasic substrate is formed of a release medium joined to a capture medium located downstream of the release medium. The release and capture media preferably comprise two different materials, or phases, having different specific characteristics. The two phases are joined together to form a single fluid path such that a solvent front can travel unimpeded from the proximal (upstream) end of the release medium to the distal (downstream) end of the capture medium.

For tests such as those described above, visually observable indicia can be preferred. Such indicia can be provided in a digital form (e.g., a digital readout on a liquid crystal display (LCD) or similar screen). Alternatively, such indicia can be provided in an analog form, which typically has included the presence of agglutination or a color change at a defined site on the assay. While digital indicia can provide improved ease of reading the test result, such digital diagnostic test devices can have increased expense and increased opportunity for failure of the electronic readout. Analog tests can be more reliable with less opportunity for malfunction; however, analog tests can suffer from difficulty in use because of inability to know when a sufficient sample volume has been applied and/or because of visual difficulties in viewing the analog test result signal(s). Because of these and other reasons, it would be beneficial to provide a personal use test device with improved communication between the test device and the user.

SUMMARY OF THE DISCLOSURE

The present disclosure relates to diagnostic test devices that include elements useful for carrying out an assay and for providing information related to the assay in a display. In an example embodiment, a pregnancy test device can be provided and can include elements for carrying out a test on a fluid sample applied to a receiving member so as to identify the presence of human chorionic gonadotropin (hCG) in the sample that is indicative of a pregnancy status. Test devices according to the present disclosure can provide for increased communication from the test device to a user thereof and make the test device easier for the user to operate, improve understanding of the results of the included assay, and increase user comfort with the test device and user assurance in the reliability of the test device.

Test devices according to the present disclosure in particular can incorporate one or more digital features that improve the use of the device and/or improve the interpretation of the test results provided by the device. The one or more digital features can allow for the test result to be provided in an analog form if desired to reduce the overall cost of the test device and maintain simplicity of the device while still providing the improvements arising from the inclusion of the one or more digital features. For example, the test devices may incorporate one or more of a fluid sensor, a timer, a light, and a memory component. The test devices can further include one or more control components and one or more power sources to facilitate execution of the digital functions to improve interpretation of the analog test result(s).

In one or more embodiments, the present disclosure can particularly relate to a diagnostic test device comprising: a housing having a viewing window; a sample receiving member extending between a proximal end positioned within the housing and a distal end extending outward from the housing; a test member positioned within the housing, the test member extending between a distal end in fluid communication with the proximal end of the sample receiving member and a proximal end such that a portion of the test member is visible through the viewing window; a fluid sensor in communication with the sample receiving member and configured to provide a signal; a power source; a light source configured to provide illumination that is externally visible; and a control component configured to automatically supply power from the power source to the light source for one or more time periods after receiving the signal from the fluid sensor. In further embodiments, the diagnostic test device can be further defined in relation to one or more of the following statements, which can be combined in any number and order.

The test member can comprise a release medium in fluid communication with a capture medium, and wherein a portion of the capture medium is visible through the viewing window.

The test device can be configured to detect the presence of an analyte in a fluid sample applied to the sample receiving member.

The presence of the analyte can be indicated by an analog signal that is visible through the viewing window.

The analyte can be selected from the group consisting of human chorionic gonadotropin (hCG), luteinizing hormone (LH), follicle stimulating hormone (FSH), thyroid stimulating hormone, estrogen, progesterone, testosterone, a metabolite thereof, and combinations thereof.

At least the portion of the test member that is visible through the viewing window can be light permeable.

The fluid sensor can be configured as an electrical circuit that includes the sample receiving member.

The fluid sensor can include a pair of electrical contacts that are physically separated and are in contact with the sample receiving member.

The pair of electrical contacts can be in electrical connection with the control component.

The fluid sensor i can be s configured to signal that a fluid applied to the sample receiving member is present at a suitable volume for the test device to carry out a specified test.

The light source can be positioned inside the housing such that the test member is between the light source and the viewing window.

The source can include a light emitting diode (LED) and a light guide.

The LED can be positioned so as to be off-set from the viewing window, and wherein the light guide is configured to transmit light from the LED to the viewing window.

The light guide can define an illumination zone positioned inside the housing such that the test member is between the illumination zone and the viewing window.

The light source can be visible through the viewing window.

The light source can be visible through a section of the housing.

The control component can be configured to execute one or more functions after receiving the signal from the fluid sensor, said one or more functions being effective to provide indicia to a user that a sufficient volume of a fluid sample has been applied to the sample receiving member.

The one or more functions can comprise supplying power from the power source to the light source for a pre-set time period.

The control component can include a timer.

The control component can be configured to supply power from the power source to the light source for one or more pre-set time periods measured by the timer.

The control component can be configured to supply power from the power source to the light source for a first pre-set time period and a second pre-set time period, the first pre-set time period and the second pre-set time period being non-overlapping.

The first pre-set time period can be activated by the signal from the fluid sensor.

The second pre-set time period can be activated based upon passing of an estimated time for completion of a test that the diagnostic test device is configured to carry out.

The control component can be configured to supply power from the power source to the light source such that the light source provides one or more blinking effects.

In one or more embodiments, the present disclosure further can relate to methods for improving ease of use of a diagnostic test device. For example, such methods can comprise: preparing the test device to include: a housing having a viewing window; a sample receiving member extending outward from the housing; a test member positioned within the housing so as to be in fluid communication with the sample receiving member and such that a portion of the test member is visible through the viewing window; a fluid sensor in communication with the sample receiving member and configured to provide a signal; a power source; a light source configured to provide illumination through the viewing window; and a control component; and configuring the control component to: provide one or more indicia to a user that a sufficient volume of a fluid sample has been applied to the sample receiving member; and automatically supply power from the power source to the light source upon passing of an estimated time for completion of a test that the diagnostic test device is configured to carry out. In further embodiments, the methods can be further defined in relation to one or more of the following statements, which can be combined in any number and order.

The one or more indicia can comprise supplying power from the power source to the light source for a pre-set time period.

The test device can be configured to detect the presence of an analyte in a fluid sample applied to the sample receiving member and provide an analog signal that is visible through the viewing window.

Visibility of the analog signal can be improved by the presence of the illumination through the viewing window provided by the light source upon the passing of the estimated time for completion of the test that the diagnostic test device is configured to carry out.

BRIEF DESCRIPTION OF THE DRAWINGS

The present disclosure is particularly described in reference to the following figures; however, such figures are provided to illustrate only preferred embodiments of the disclosure, and the disclosure is not intended to be limited thereto.

DETAILED DESCRIPTION OF THE DISCLOSURE

The present disclosure now will be described more fully hereinafter with reference to specific embodiments and particularly to the various drawings provided herewith. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

In one aspect, the present disclosure relates to a test device, such as an over-the-counter (OTC) or point of care (POC) test device, for detecting an analyte in a sample. The device generally includes components suitable for carrying out an assay, such as a lateral flow assay, and also includes components suitable for communicating information relating to the assay to an individual.

The test components in a broad sense can comprise a proximal portion (e.g., a sample receiving member) in fluid communication with a distal portion (e.g., a reservoir). The proximal and distal portions may be interconnected by a substrate material, which itself may form all or part of the proximal and/or distal portion of the device. A sample (e.g., urine) can be directly or indirectly applied to the proximal portion of the device for transport to the distal portion. Preferably, the sample flows across the substrate so as to contact one or more antibodies attached to or otherwise deposited on the substrate. The antibodies can be designed and/or chosen to recognize a variety of analytes. In specific embodiments, a test device according to the present disclosure can be useful for detection of human chorionic gonadotropin (hCG), luteinizing hormone (LH), follicle stimulating hormone (FSH), thyroid stimulating hormone, estrogen, progesterone, testosterone, a metabolite thereof, and combinations thereof. Even further analytes also can be encompassed by the present disclosure.

The devices disclosed herein can make use of a variety of techniques for detecting the presence of an analyte. One example is a sandwich technique wherein one or more antibodies used in the detection comprise a binding member or site which binds to an epitope on the analyte for detection. A labeled antibody binds to the analyte to form a complex in the sample. The analyte, which is bound to the labeled antibody or antibodies, binds with one or more capture antibodies to form a "sandwich," comprising the capture antibody, analyte (or antigen), and the labeled antibody. Each sandwich complex thus produced comprises three components: one capture antibody, one antigen, and one labeled antibody. An antibody used herein can be a polypeptide substantially encoded by an immunoglobulin gene or immunoglobulin genes, or fragments thereof, which may specifically recognize and bind an antigen. The recognized immunoglobulin genes include the kappa, lambda, alpha, gamma, delta, epsilon, and mu constant region genes, as well as the immunoglobulin variable region genes. Antibodies include fragments, such as Fab', $F(ab)_2$, Fabc, and Fv fragments. The term antibody also can include antibody fragments either produced by the modification of whole antibodies or those synthesized de novo using recombinant DNA methodologies, and further can include "humanized" antibodies made by conventional techniques. Although polyclonal antibodies can be used, antibodies are preferably monoclonal antibodies. A capture antibody according to the disclosure can be an antibody attached to a substrate directly or indirectly, such as a solid substrate. The capture antibody can include at least one binding member that specifically or preferentially binds a particular distinct epitope of an antigen.

In the sandwich technique, the makeup of each sandwich complex can vary depending upon the particular labeled antibody (and thus the particular antigen) included therein. In the same test, there can be multiple different types of sandwiches produced. The sandwich complexes are progressively produced as the test sample with the analyte therein continuously moves along the substrate of the device. As more and more of the analyte/labeled antibody complex is immobilized in sandwich form with the capture antibody or antibodies at the capture site, the label components aggregate and become detectable in that the accumulation of the sandwich complexes at the capture site can be detected in various ways, such as by visual inspection of, for example, color development at the capture site (i.e., an "analog" test result) or by a digital readout resulting from the electronic analysis of the aggregate at the capture site as further described herein. Although the sandwich technique is provided as an exemplary embodiment, the devices described herein in relation to the improved communication aspects are not limited to such underlying technique. Rather, other techniques for identifying an analyte in a test sample and forming a detectable signal based on the presence or absence of the analyte in the sample can be utilized.

Exemplary means for forming a detectable signal can comprise the use of a conjugate comprising one or more antibodies bound to detectable label components (e.g., colored particles, such as a metal sol or colloid particles). One or more of the antibodies used in the disclosed devices (e.g., one or two) can be labeled. Any detectable label recognized in the art as being useful in various assays can be used. In particular, the detectable label component can include compositions detectable by reflective, spectroscopic, photochemical, biochemical, immunochemical, or chemical means. As such, the label component produces a detectable signal. For instance, suitable labels include soluble dyes, fluorescent dyes, chemiluminescent compounds, radioisotopes, electron-dense reagents, enzymes, colored particles, or dioxigenin. The label component can generate a measurable signal, such as radioactivity, fluorescent light, color, or enzyme activity, which can be used to identify and quantify the amount of label bound to a capture site. Thus, the label component can also represent the presence or absence of a particular antigen bound thereto, as well as a relative amount of the antigen (e.g., relative to a known standard, threshold standard, or a different standard). The test devices of the present disclosure can be particularly configured to provide an analog test result wherein the test result is interpreted by a user of the device by visual inspection of the analog result. In particular, the analog result can be formation of a colored section of a test strip, a colored line, a colored symbol, or the like. Devices configured for providing an analog test result can be cheaper and/or simpler to manufacture and can exhibit less opportunity for malfunction due to a problem with electronic components. The presently disclosed devices can thus be specifically adapted to improve the ability to interpret an analog test result. If desired, however, in some embodiments, one or more aspects of the present disclosure may be utilized in a test device that is configured to provide a digital result. In such embodiments, the labeled materials can be detected through use of suitable electronic components, including hardware and software, and thus can be communicated to a user via digital signal or similar means. Further detail regarding the production of digital signals in personal use assays is provided, for example, in U.S. Pat. No. 7,214,542 to Hutchinson; U.S. Pat. No. 7,220,597 to Zin et al.; and U.S. Pat. No. 7,499,170 to Sasaki et al., which are incorporated herein by reference.

Devices according to the present disclosure can include one or more standards or internal controls that allow for determination of whether signal development is a true indication of the presence or absence of analyte in the sample or is simply an artifact, such as caused by nonspecific sorption. For example, a negative control site can be prepared identically to the test site, except that immobilization of the capture antibody is omitted. Therefore, although the conjugate will reach the negative control site, it will aggregate due only to non-specific binding. Similarly, the device can include a positive control, such as with an authentic sample of the analyte for detection immobilized at the positive control site. An alternate control site can be located downstream of the capture site and have immobilized thereon at least one capture antibody (e.g., a protein). Such control site can function to capture and immobilize labeled antibody which has not been captured at the capture site. For example, such control site can include polyclonal antisera specific for the labeled antibody immobilized thereon to indicate proper functioning of the assay.

In some embodiments, a biphasic chromatographic medium (substrate/test strip) can be used in the disclosed assays and can comprise an upstream release medium joined to a downstream capture medium. The release and capture media can comprise two different materials or phases having different specific characteristics. The two phases can be joined together to form a single fluid path such that a solvent front can travel unimpeded from the proximal (upstream) end of the release medium (which can be defined as a proximal portion of the biphasic medium) to the distal (downstream) end of the capture medium (which can be defined as a distal portion of the biphasic medium). A sample receiving member can be generally provided at the proximal end of the biphasic substrate and a reservoir of sorbent material can be located beyond the biphasic substrate.

In other embodiments, a triphasic chromatographic medium (substrate/test strip) can be used in the disclosed assays and can comprise a capture medium overlapped at one end by a release medium and at the opposing end by a reservoir. The triphasic substrate can be in fluid communication with a sample receiving member at the end thereof comprising the release medium.

In certain embodiments, use of a biphasic or triphasic chromatographic medium may enhance the speed and sensitivity of an assay, such as those described in U.S. Pat. Nos. 6,319,676, 6,767,714, 7,045,342, and U.S. Publication No. 2012/0083044, which are incorporated herein by reference, including without limitation for the purpose of describing biphasic and triphasic chromatographic media. Methods for manufacturing chromatographic media are also described in detail in U.S. Pat. No. 5,846,835, the disclosure of which is incorporated herein by reference in its entirety.

Reagents for detecting, labeling, and capturing an analyte of interest can be disposed on the release and capture media. In certain embodiments, one or more labeled conjugates can be located on the release medium and each can include a binding member (e.g., antibody) that may be reactive with a particular site (sometimes referred to as a "first epitope," "second epitope," etc.) on the analyte of interest. The labeled conjugates further can comprise one or more detectable markers (or labels), as discussed herein.

The release medium can be formed from a substance which allows for release of reagents deposited thereon, which can comprise reagents that are releasably (i.e., not permanently) bound to the release medium. The primary function of the release medium is first to support and to subsequently release and transport various immunological components of the assay, such as a labeled conjugate and/or a capturable conjugate, both of which are capable of binding to the analyte of interest. The release medium can be formed of any material capable holding, releasing, and transporting various immunological parts of the test such as the labeled test component (e.g., a bibulous, hydrophilic material).

The capture medium can be formed from a material which permits immobilization of reagents for detection of the presence of analyte in the test fluid. Immobilization can refer to any interaction that results in antibodies or analytes being irreversibly bound to the substrate such that they are not appreciably washed away, e.g., during the course of a single use of the device. The capture medium can comprise hydrophilic polymeric materials, such as microporous films or membranes, which permit protein reagents to be immobilized directly on the membrane by passive adsorption without the need for chemical or physical fixation, although fixation is not necessarily excluded.

The release medium and capture medium can be joined via any suitable means. For example, the two media can be joined by overlapping the downstream edge of the release medium over the upstream edge of the capture medium. The various media components of the biphasic or triphasic substrate can be adhered to a clear polymer film or opaque sheet, thereby holding the media in place. Alternately, the media can be connected by a non-overlapping butt joint and may still be attached to an underlying support.

The diffusible and non-diffusible reagents can be applied to the release and capture media, respectively, by any suitable technique. In one embodiment, the diffusible antibody reagents can be applied to the release medium by direct application onto the surface of the medium and dried to form a band. Generally, reagents can be immobilized using absorption, adsorption, or ionic or covalent coupling, in accordance with any suitable methods.

Figure 1:
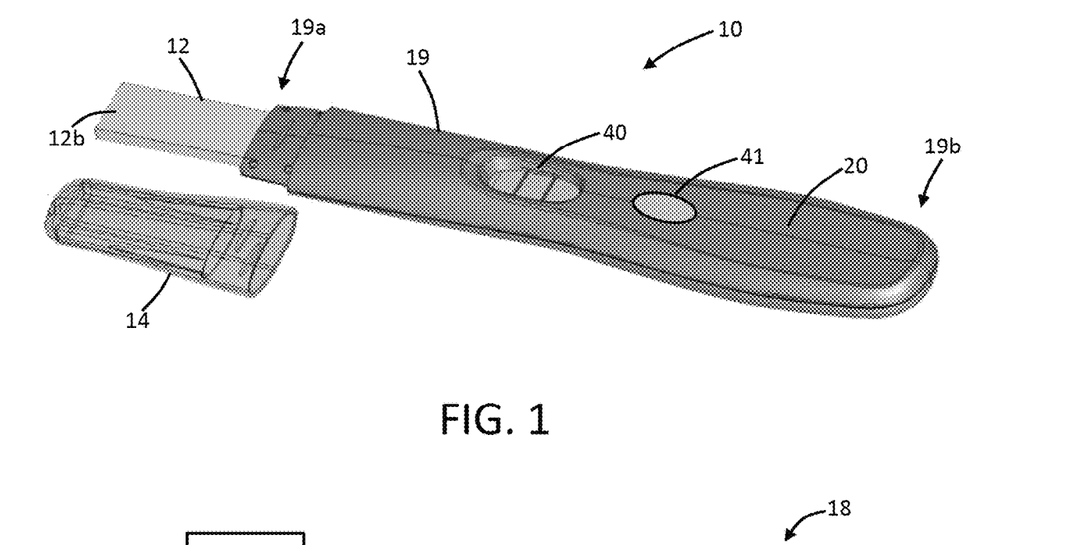
FIG. 1 is a perspective view of a test device according to an example embodiment of the present disclosure.

In one embodiment, a test device 10 according to the present disclosure can comprise a housing defining a sample inlet, a test volume, and reservoir volume, as illustrated in FIG. 1. The housing 19 can include a sampling end 19a and a holding end 19b, which can include a recessed portion 20 shaped to permit users to place their thumb into the recessed portion and their forefinger on the bottom of the housing to securely hold the test device 10. Disposed within the housing 19 are the functional components forming a test member. The test member can be a single strip or a combination of strips of materials useful for providing an assay. For example, the test member can be a test strip as described herein, such as comprising a biphasic or triphasic substrate, for use in an assay. A sample receiving member 12 can be disposed partially within the housing 19, extend outward therefrom, and may be covered by a removable cap 14. More particularly, the sample receiving member 12 can extend between a proximal end 12a positioned within the housing 19 and a distal end 12b extending outward from the housing. The test member 18 likewise can extend between a distal end 18b in fluid communication with the proximal end 12a of the sample receiving member and a proximal end 18a such that a portion of the test member 18 is visible through a viewing window 40 formed in the housing 19.

In use, a test sample passes from the sample receiving member 12 to the test member 18, such as a chromatographic substrate, where the sample is in reactive contact with the test site (e.g., the capture site), and optionally one or more control sites. A viewing window 40 on the top of the casing 19 defines a region that permits a user to observe test results as they become detectable. As described herein, "becoming detectable" specifically can relate to the accumulation of sandwich complexes at the capture site, which can be detected in various ways, such as by visual inspection of color formation within the viewing window 40 as an analog test result. This specifically can be the aggregate at the capture site as further described herein. In the embodiment illustrated, the viewing window 40 can provide for viewing of the analog signal, such as a colored indicator of accumulation of labeled complexes at the test site visible through the viewing window. Further, components necessary to form an electronic communication circuit can be retained with the casing of the test device, as otherwise described herein.

In the use of one exemplary assay, a sample passes through the inlet defined by the sample receiving member 12 and into the interior of a housing 19, where it comes into contact with the test member 18 including a release medium 30 and a capture medium 32. If the analyte of interest is present in the sample, it binds to the one or more labeled antibodies which are releasably attached to the release medium 30. The sample, now comprising analyte-labeled antibody conjugates, wicks up the release medium 30 and forms a sandwich complex with one or more capture antibodies immobilized on the capture medium 32 (defining a capture site or test site). As the sample front passes across the capture site, a complex is formed comprising the analyte, labeled antibody, and the capture antibody. This "sandwich" complex can be analyzed by detecting the presence of the label at the capture site. Detection particularly can be via a visual review of a formed color in the viewing window as an analog signal. If desired, however, detection may include, at least in part, a digital readout on, for example, an LCD (liquid crystal display) screen. Although the present disclosure is described largely in terms of direct devices/direct detection, other devices (i.e., affinity-based devices) are also intended to be encompassed herein. Affinity-based devices operate on similar principles, but rely on indirect binding (wherein one member of an affinity pair (e.g., biotin) is present on a capturable conjugate (and subsequently on any diffusible sandwich complex formed therefrom) and the other member of the affinity pair (e.g., avidin) is present on the capture medium section of the substrate).

Figure 2:
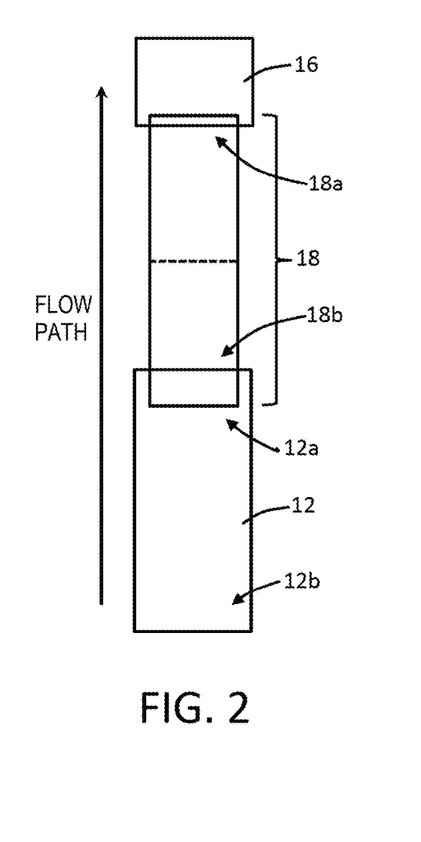
FIG. 2 shows a top view of lateral flow test components according to one example embodiment of the present disclosure comprising a reservoir absorbent material, a biphasic substrate, and a sample receiving member.

FIG. 2 shows an example of lateral flow test components that can be present in a device 10 such as illustrated in FIG. 1. These test components can comprise a sample receiving member 12, biphasic chromatographic substrate 18, and reservoir absorbent material 16. When the device is placed in contact with a fluid sample, the fluid is transported by capillary action, wicking, or simple wetting along the flow path downstream through sample receiving member 12, along chromatographic substrate 18, and into reservoir absorbent material 16, generally as depicted by the arrow. Sample receiving member 12 may also serve as a filter which can remove particulate matter and interfering factors from a sample. The sample receiving member 12 preferably is a bibulous hydrophilic material which facilitates absorption and transport of a fluid sample to the biphasic chromatographic substrate 18. Such materials may include cellulose acetate, hydrophilic polyester, or other materials having similar properties. A combination of absorbent materials also may be used. As noted above, a filtration means which limits the introduction to the test site of contaminants from the sample may also be included. In certain embodiments, the sample receiving member 12 can be omitted, and the release medium of a biphasic substrate 18 can itself act as the sample receiving member. Such embodiments of the assay materials are useful in performing dipstick assays. By providing a reservoir of sorbent material (e.g., absorbent paper made form cotton long linter fibers or cellulosic materials) disposed beyond the chromatographic substrate, a relatively large volume of the test fluid and any analyte it contains can be drawn through the test area to facilitate background clearance and thereby aid sensitivity. The reservoir absorbent generally facilitates capillary action along the chromatographic substrate and absorbs excess fluid contained within the device.

Figure 3:
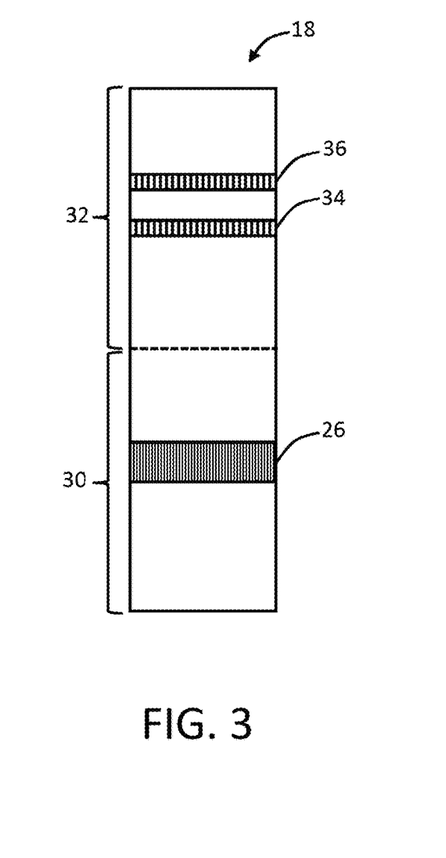
FIG. 3 shows a top view of a biphasic substrate for use in a test device according to an example embodiment of the present disclosure.

FIG. 3 illustrates in greater detail an exemplary biphasic chromatographic substrate 18, comprising a release medium 30 and a capture medium 32 joined together to form a single fluid path. A band 26 of labeled binding member, e.g., an antibody-metal sol, can be releasably disposed on the release medium 30. In one embodiment, the labeled binding member is in dehydrated form. As the fluid sample moves past the band 26, the labeled binding member becomes entrained in the fluid, reconstituted (in the case of a dehydrated binding member), and binds with a particular analyte or analytes of interest present in the fluid sample. Accordingly, the resulting complex comprising a binding antibody, a label component, and an analyte for identification (e.g., hCG) advances along with the sample front until it reaches the capture site 34. In this particular embodiment, the capture site includes at least one immobilized capture antibody which binds to a different epitope of the analyte. Accordingly, a sandwich complex including the desired analyte is formed at the capture site 34. If desired, a control site 36 can be present. As can be seen in FIG. 1, a portion of the capture medium (particularly a portion including at least the capture site) is visible through the viewing window 40.

For further detail regarding various testing devices, methods of use, and parameters thereof, see for example U.S. Pat. Nos. 5,739,041; 6,046,057; 6,277,650; 6,319,676; 6,767,714; 7,045,342, 7,763,454; 7,776,618 and 8,211,711 to Nazareth et al., and U.S. Patent Application Publication Nos. 2002/0042082, 2004/0171174; 2008/0213920; 2010/0051350; 2010/0239460; 2010/0240149; 2010/0261293; 2010/0267166; and 2011/0201122 to Nazareth et al., and 2012/0083044 to Sturman et al.; which are incorporated herein by reference in their entireties.

Figure 4:
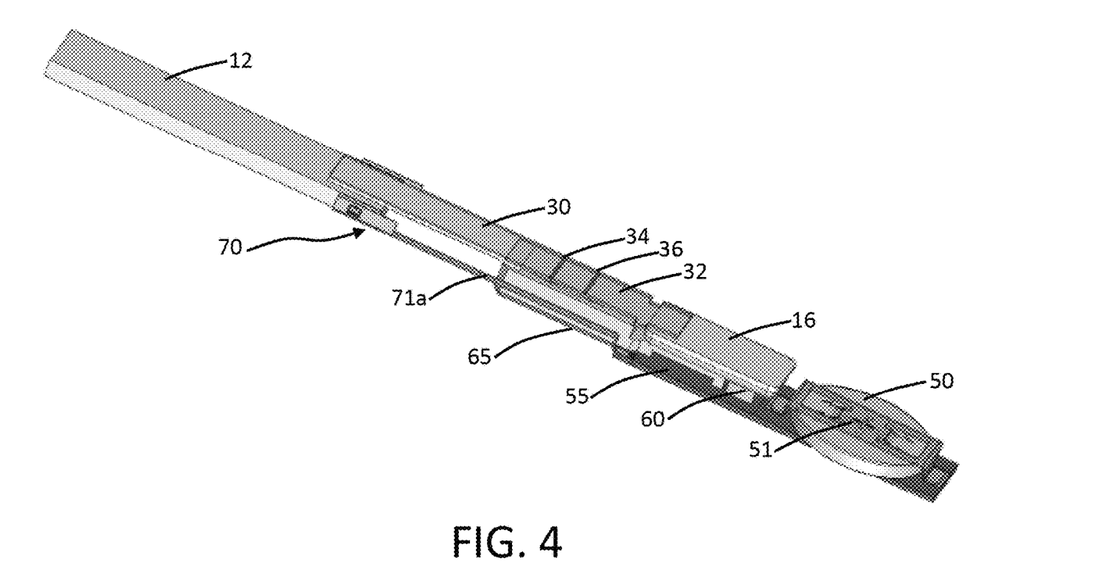
FIG. 4 shows a perspective view of the internal components of a test device according to an example embodiment of the present disclosure.

In addition to the test member, the present devices can incorporate one or more components configured to impart one or more digital functions that can improve the ability of a consumer to use the device and/or improve the ability of a consumer to visualize the analog test result. For example, FIG. 4 shows internal components of a test device according to an example embodiment with the housing removed. As seen therein, the test device can include a power source which, as illustrated, is a battery 50 with a positive contact 51 and a negative contact (not visible) present on a printed circuit board (PCB) 55. One or a plurality of batteries may be utilized. Alternatively, or additionally, the power source may comprise a capacitor or other suitable element.

One or more control component(s) 60 likewise may be included in the test device and particularly can be positioned on the PCB 55. The control component 60 may, in some examples, include electronic components such as processing circuitry configured to perform data processing, application execution, or other processing, control, or management services according to one or more example implementations. The processing circuitry may include a processor embodied in a variety of forms such as at least one processor core, microprocessor, coprocessor, controller, microcontroller, or various other computing or processing devices including one or more integrated circuits such as, for example, an ASIC (application specific integrated circuit), an FPGA (field programmable gate array), some combination thereof, or the like. In some examples, the processing circuitry may include memory coupled to or integrated with the processor, and which may store data, computer program instructions executable by the processor, some combination thereof, or the like. A control component 60 may be adapted to or configured to carry out one or more functions as further described herein and may specifically interact with one or more components of the test device to provide one or more digital functions.

In one or more embodiments, the test device can include a fluid sensor 70, which may be a single component or may be a combination of multiple components that function as a unit. The fluid sensor 70 preferably is configured to provide a signal that can be delivered to and interpreted by one or more further components of the test device. For example, the fluid sensor 70 may be in communication (wired or wirelessly) with the one or more control component(s) 60 such that a signal from the fluid sensor may be interpreted by the control component and, optionally, be utilized for eliciting one or more further functions by the test device. The fluid sensor 70 (or at least one component of the fluid sensor) preferably is in communication with one or more components of the test device configured for liquid transport. This may include, for example, the sample receiving member 12, the release medium 30, the capture medium 32, and/or the reservoir 16. If desired, a plurality of fluid sensors may be in communication with a plurality of components of the test device to provide a plurality of signals that may be combined or separately interpreted by the control component 60 for executing one or a plurality of functions. In some embodiments, the communication may be physical contact between the fluid sensor 70 (or at least one component of the fluid sensor) and one or more components of the test device.

Figure 5:
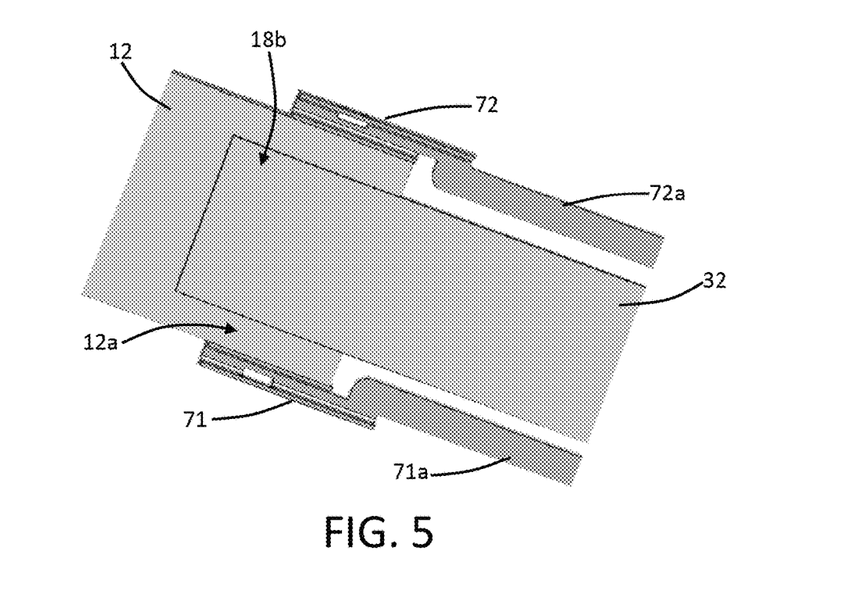
FIG. 5 shows an enlarged view of a section of the internal components of a test device according to an example embodiment of the present disclosure.
Figure 6:
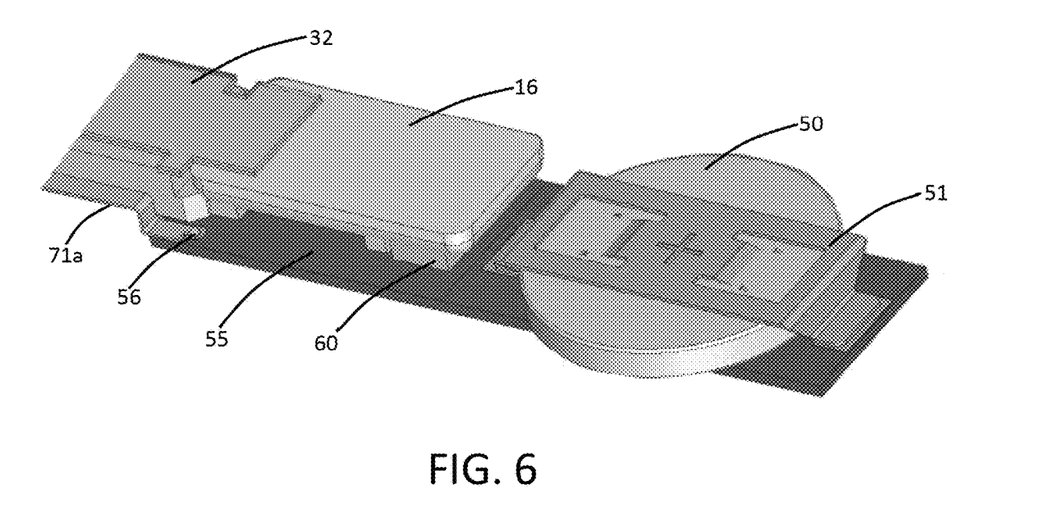
FIG. 6 shows an enlarged view of a further section of the internal components of a test device according to an example embodiment of the present disclosure.

An example embodiment of a fluid sensor 70 is illustrated generally in FIG. 4 and shown in greater detail in FIG. 5. As seen therein, the fluid sensor comprises a pair of electrical contacts (71, 72) that are physically separated and are in contact with the sample receiving member 12. The pair of electrical contacts (71, 72) specifically can be configured to be in electrical connection with the control component 60 and/or the power source 50. As illustrated in FIG. 4 and FIG. 5, the electrical contacts 71 and 72 each include an electrical extension 71a and 72a, respectively, that extends to be in direct connection with the PCB 55 (e.g., attached to electrical connectors 56 on the PCB—see FIG. 6). Alternatively, the electrical contacts 71 and 72 may be in a wired connection with the PCB 55 wherein electrical wires are connected at opposing ends to an electrical contact (72, 72) and the PCB. In some embodiments, the fluid sensor specifically can be configured as an electrical circuit that includes the sample receiving member 12. More particularly, the electrical contacts (71, 72), the electrical extensions 71a and 72a (or alternative connectors) suitable electrical circuits present on the PCB (e.g., the control component 60 and the battery 50, as well as any printed circuitry) can form an open electrical circuit with the sample receiving member 12 essentially functioning as a switch. When the sample receiving member is substantially dry, no electrical current may flow between the electrical contacts (71, 72), but once a liquid sample is applied to the sample receiving member 12, the liquid bridging the electrical contacts (71, 72) can close the circuit and thus cause current to flow through the electrical circuit. The establishment of electrical current flow through this electrical circuit then can function as the signal that is provided by the fluid sensor. Although this is described in relation to the sample receiving member 12, it is understood that other portions of the test device that are configured for passage of liquid (e.g., the release medium 30, the capture medium 32, and/or the reservoir 16) may similarly function as part of an electrical circuit and thus as part of a fluid sensor.

When the sample receiving member is utilized as discussed above, the fluid sensor thus can be configured to signal that a fluid applied to the sample receiving member is present in a suitable volume for the test device to carry out a specified test. Other analog test devices that function by liquid transport across a medium can fail to provide a completed test if an insufficient volume of liquid is applied to the test medium. For example, the distal end 12b of the sample receiving member 12 may appear wetted, but it may be difficult to determine if the portion of the sample receiving member positioned inside of the device housing 19 is fully wetted. By placing the electrical contacts (71, 72) at or near the proximal end 12a of the sample receiving member, the fluid sensor will only be activated if a sufficiently volume of the liquid sample is applied to the sample receiving member to wick up to and substantially fill the proximal end of the sample receiving member 12. Because of the overlap of the sample receiving member 12 and the release medium 30, if a sufficient volume of liquid sample is present to fully wick to the proximal end 12a of the sample receiving member, it can be determined to be a sufficient volume of sample to wick across the test strip and complete the test. As further described below, initiation of a signal from the fluid sensor can be used to cause one or more further functions of the test device to be carried out.

In one or more embodiments, the test devices of the present disclosure can include one or more light source(s). An individual light source may be configured to provide a single color of light or a plurality of different light colors. A single light source may be utilized to provide a lighting effect to a single portion of the test device, or a single light source may be utilized to provide a lighting effect to a plurality of different portions of the test device at the same time or at different times. A light source may include any component effective for providing light output and particularly may include one or more light emitting diodes (LED). For example, a single LED may be present and may be configured for emitting light of a single color (e.g., white light, red light, etc.) or may be configured for emitting light of multiple, different colors. For example, an RGB LED may be used so that light in red, blue, and green colors may be emitted and may be mixed as needed to emit a wide variety of different colors. In other embodiments, a plurality of LEDs (e.g., two, three, four, or more) may be included in the device, and individual LEDs may be configured to emit a single color or a plurality of colors.

Figure 7:
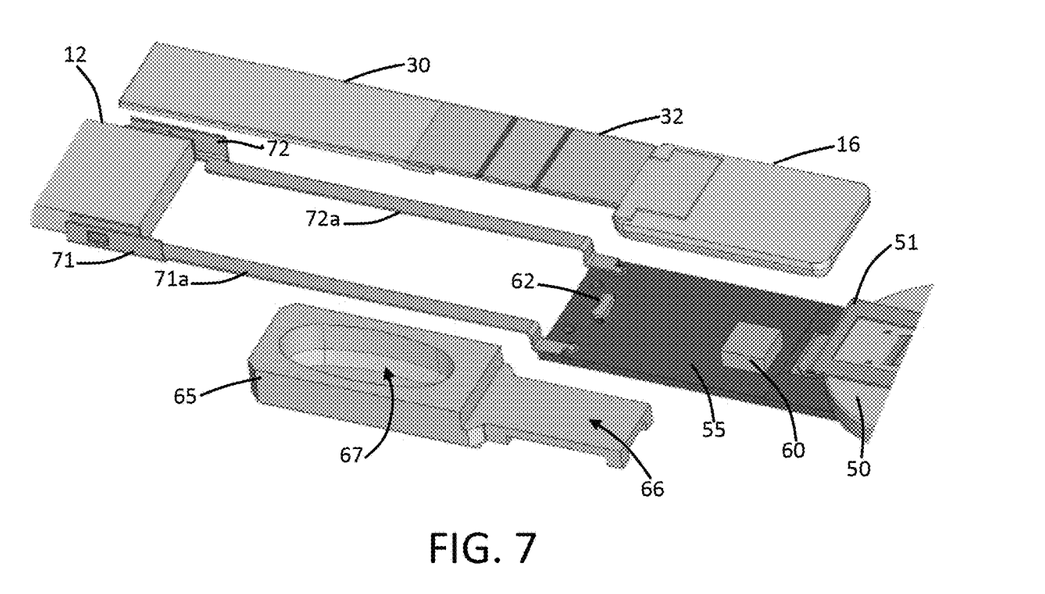
FIG. 7 shows a partial view of the internal components of a test device according to the present disclosure in a partially exploded condition.

In some embodiments, a light source can be configured to provide illumination that is configured to be visually evident external to the housing 19. For example, in some embodiments, a light source can be configured to provide illumination specifically through the viewing window of the test device. This may be achieved through a variety of configurations. For example, as seen in FIG. 7, the light source may comprise an LED 62 that is positioned directly on the PCB 55. If desired, however, the LED 62 may be present elsewhere in the test device and may be electrically connected to the PCB 55 via appropriate electrical wiring.

The light source in particular may be positioned inside the housing 19 such that the test member 18 is between the light source and the viewing window 40. This can be particularly beneficial when the light source is configured for providing lighting through the viewing window 40. In such embodiments, at least the portion of the test member 18 that is visible through the viewing window 40 can be light permeable. For example, the capture medium 32 may be configured to be light permeable such that illumination behind the capture medium can improve viewing the test results (e.g., color formation at the capture site 34). In other embodiments, the test member 18 may be substantially impermeable to light, but the test member and the housing 19 may be size such that illumination behind the test member is visible around the edges of the test member such that the viewing window 40 is still illuminated by the light source, and the viewing of the test results may still be improved.

In some embodiments, the light source may include both of an LED 62 and a light guide 65. The use of a light guide 65 can allow for placement of the LED 62 directly on the PCB 55 while still providing illumination at a site distant from the PCB. Referring to FIG. 7, internal components of the test device are shown in part with certain components being displaced for ease of viewing. Specifically, when assembled, the light guide 65 is positioned such that a shield section 66 is positioned over the LED 62. The shield section 66 may be specifically configured to substantially or completely block light transmission therethrough (e.g., being opaque). As seen in FIG. 7, a bottom portion of the shield section 66 is open such that light from the LED 62 may pass therethrough to other portions of the light guide 65. The light guide 65 extends away from the LED 62 and toward the sample receiving member 12. The combined release medium 30, capture medium 32, and reservoir 16 are then positioned over the light guide 65. As illustrated, the light guide 65 further defines an illuminable chamber 67 and, when fully assembled, the test member 18 (and particularly the capture medium 32, in some embodiments) is between the illuminable chamber and the viewing window 40 formed in the housing 19. The illuminable chamber 67 therefore illustrates one embodiment of an illumination zone that may be present in the housing. As further discussed below, one or more illumination zones may be provided at a variety of locations in the housing by a variety of configurations.

In some embodiments, the LED 62 may be positioned laterally relative to the viewing window 40 such that the light guide 65 is configured to transmit light from the LED 62 to the viewing window. The presence of the illuminable chamber 67 can be useful to provide a glowing effect through the viewing window 40. Such lateral positioning is intended to encompass any configuration wherein the light emitting element (e.g., the LED 62) is not positioned directly within the field of view where the light is externally visual. Thus, lateral positioning can indicate that the light emitting element is positioned rearward, forward, sideways, or in any direction so as to be off-set from the viewing window 40 or from any other section of the device wherefrom the light is intended to be visually evident.

In other embodiments, the light guide 62 may take on different construction. For example, the light guide may be substantially in the form of an elongated member with any desired cross-sectional shape (e.g., round, square, triangular, etc.) and may be configured to transmit light to a variety of positions in the test device. For example, the light guide 62 (optionally in a different form than illustrated) may extend a further distance toward the sample receiving member 12 such that light may define an illumination zone that can be visible through the sampling end 19a of the housing 19.

Figure 8:
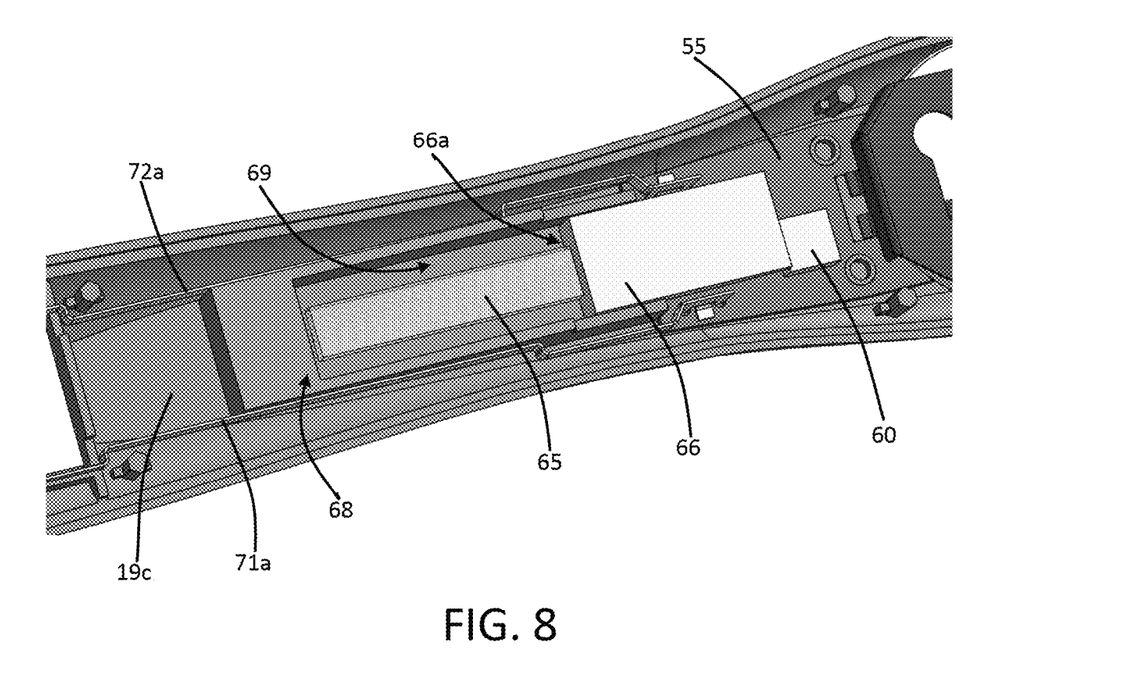
FIG. 8 shows a partial view of a portion of the internal components of a test device according to an example embodiment of the present disclosure.

As a further example, FIG. 8 illustrates an embodiment wherein the housing 19 is configured to define a well 69 in a bottom portion thereof. The well 69 in particular may be defined at least in part by a plurality of walls 68 rising upward a distance from an interior surface of a bottom portion 19c the housing 19. In the example embodiment, a shield section 66 is again positioned over the LED, and the shield section can be translucent so that light transmission is limited or can be opaque so that light transmission is completely occluded. The shield section 66 includes an opening 66a therein, and a light guide 65 extends outward from the opening. The light guide 65 is positioned within the well 69 defined by the walls 68, and this therefore can create a further option for an illumination zone within the device. As before, the test member 18 (and particularly the capture medium 32, in some embodiments) can be positioned between the well 69 and the viewing window 40 formed in the housing 19 so that light from the light guide 65 may shine therethrough. In some embodiments, one or more surfaces forming the well (e.g., the walls 68 and/or the bottom surface 19c of the interior of the housing 19) may be configured to improve illumination of the light guide. For example, one or more of such surfaces may be provided with a light reflective finish (e.g., a white color for light reflection, a mirrored finish, a metallic finish, or the like) so that light from the light guide 65 is at least partially reflected from the one or more surfaces and outward from the well 69. Such finishing may also be applied to an interior surface of the illuminable chamber 67 described above. Still further, such finishing and/or the shape of the light guide and/or the size of the light guide, and/or the positioning of the light guide may be configured to provide for substantially even illumination through the viewing window 40 or through another portion of the housing. For example, when the light guide is positioned behind the test strip, there may be a tendency for more light to pass around the test strip than to pass through the test strip. As such, the light guide may be positioned to be more centrally located in the viewing window so that the intensity of the light is greater directly behind the test strip. In this manner, light passing around the test strip may be perceived to be more evenly distributed with the light passing through the test strip. Likewise, the application of the finish to the well as described above can likewise be utilized for such purpose.

In other embodiments, the housing 19 may include one or more further openings 41 in addition to the viewing window 40, and the light source may be configured to provide illumination through the one or more further openings. Moreover, as already noted, the test device may include a plurality of light sources and/or a plurality of light guides so as to be configured to provide illumination at a plurality of sites on or through housing 19.

In some embodiments, the device may be configured such that light is visible through one or more portions of the housing in the absence of an actual opening therethrough.

Figure 9:
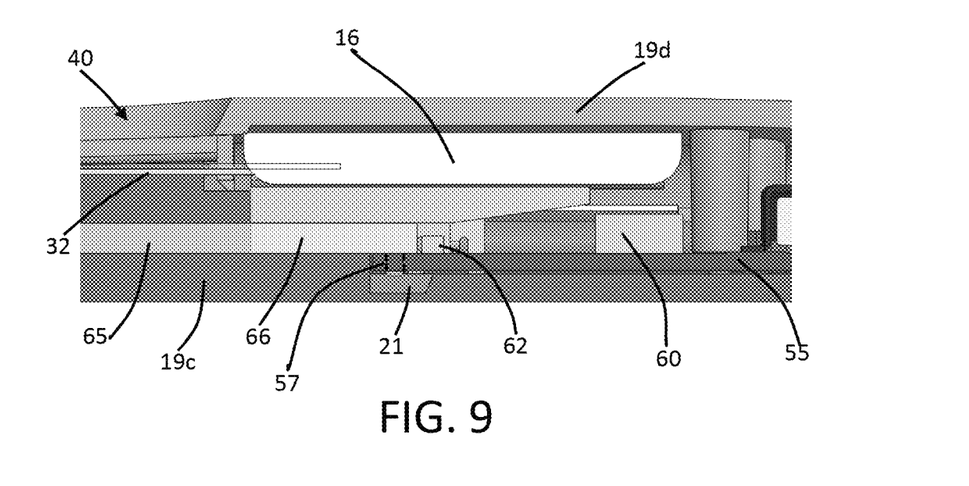
FIG. 9 shows a partial cross-sectional view of a test device according to an example embodiment of the present disclosure.

For example, one or more sections of the housing 19 may be configured to be thinned sufficiently to allow light to pass through the thinned portion. An example embodiment is illustrated in FIG. 9, which shows a partial cross-section of the device with functional components positioned between a top portion 19d and a bottom portion 19c of the housing 19. An LED 62 is positioned on the PCB 55 and configured to pass light through the light guide 65 via the shield section 66. In the illustrated embodiment, the shield section 66 has an extension 57 as defined by the dashed lines that extends through the PCB and toward a light cavity 21 defined by a thinned out section of the bottom portion 19c of the housing 19. Because the housing is thinned in the area of the light cavity 21, light is visible through the housing wall even in the absence of an actual opening. This, then, is an example of an illumination zone that does not necessarily require a physical opening in the housing for the light to be visible externally. In further embodiments, a lighting effect may be provided by other means. For example, as an alternative to the light cavity 21, or in addition to the light cavity, a series of microperforations may be provided in a portion of the housing wall so that light is visible through the microperforations. By providing for visible lighting effects through the bottom portion 19c of the housing, it is possible to provide signals of different functions of the device to a user even when the device is positioned upside down.

Figure 10:
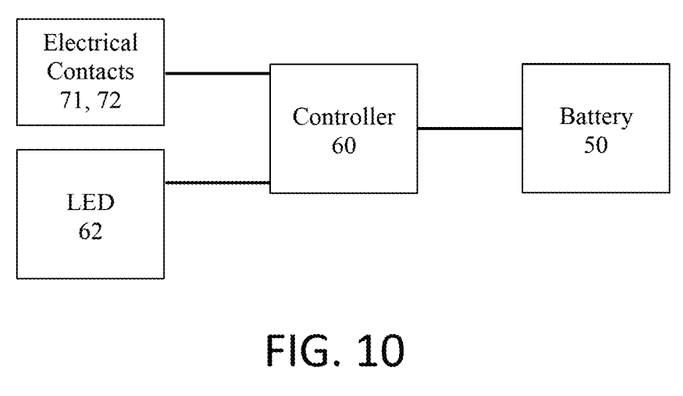
FIG. 10 is an illustration of a circuit according to an example embodiment of the present disclosure.

The control component 60 of the present test device can be configured to execute one or a variety of digital functions that can improve ease of use of the test device and/or ease of evaluation of the test result provided by the test device. For example, in some embodiments, the control component 60 can be configured to automatically supply power from the power source to the light source for one or more time periods after receiving the signal from the fluid sensor. An example embodiment of an electrical circuit 80 in the test device is shown in FIG. 10. As seen therein, the control component 60 (or controller) can be in electrical connection with all of the electrical contacts (71, 72), the LED 62, and the battery 50. The control component 60 thus may direct execution of one or more programs or programmed functions, and such functions can, in some embodiments, be reliant upon first receiving a signal from the fluid sensor (e.g., via the electrical contacts 71 and 72).

In one or more embodiments, the control component 60 may be configured to execute one or more functions to provide indicia to a user that a sufficient volume of a fluid sample has been applied to the sample receiving member 12. As noted above, the fluid sensor can be configured such that an electrical circuit is completed between the electrical contacts (71, 72) once a liquid sample applied to the sample receiving member 12 has wicked up the sample receiving member 12 a sufficient distance to contact the electrical contacts. The completion of the electrical circuit can function as a signal to the control component to supply power from the power source (e.g., the battery 50) to the light source (e.g., the LED 62) for a pre-set time period. The illumination of the light source thus can function as an indicator to the user that a sufficient volume of the liquid sample has been applied to the sample receiving member. This can substantially avoid problems associated with failing to apply a sufficient volume of the liquid sample (e.g., resulting in an incomplete test) as well as applying too much liquid sample (e.g., flooding the test device). Instructions accompanying the test device may thus state that the liquid sample is to be applied to the sample receiving member 12 until the indicator light illuminates. The user will thus be provided with clear indication that the correct volume of liquid sample has been applied to the sample receiving member and can be informed that the test can then proceed.

In embodiments where a single light source is used, the light source may be illuminated for only a limited time period. For example, light from the LED 62 may pass through the light guide 65 and illuminate the viewing window 40 of the test device for a limited period of time before turning off. As such, the control component 60 may include a timer built into the control component. The control component 60 may thus be configured to supply power from the power source to the light source for one or more pre-set time periods measured by the timer.

In embodiments where a plurality of light sources is used, the light source may again be illuminated for only a pre-set time period. Alternatively, the light source may remain illuminated throughout the test once the sensor has signaled that a sufficient liquid volume has been applied to the sample receiving member 12. For example, illumination through the sampling end 19a of the housing 19 and/or illumination through the additional opening 41 may begin once the sensor has signaled that a sufficient liquid volume has been applied to the sample receiving member 12, and such illumination may continue indefinitely.

Illumination from the light source through the viewing window 40 may be utilized to improve viewing of the test result. In embodiments wherein the view window 40 is illuminated as an indicator that a sufficient liquid volume has been applied to the sample receiving member, the viewing window may remain illuminated to provide the improved viewing of the test result. Alternatively, the control component 60 may be configured to supply power from the power source to the light source for a first pre-set time period and a second pre-set time period, the first pre-set time period and the second pre-set time period being non-overlapping. For example, lateral flow assays typically may take a time of about two to three minutes for the liquid sample to wick across the sample receiving member 12, the release medium 30, the capture medium 32, and then to the reservoir 16 to ensure that any analyte in the liquid sample accumulates at the capture site 34 to provide the test result. Thus, control component 60 may be configured to illuminate the light source for a first time period that is separated from second time period of illumination by a timer period of non-illumination. The first time period and the second time period of illumination may be substantially equal. Alternatively, the first time period and the second time period of illumination may be substantially different in length. In some embodiments, the first time period of illumination may be about 5 seconds to about 45 seconds, about 5 seconds to about 30 seconds, about 10 seconds to about 30 seconds, or about 10 seconds to about 20 seconds. This can provide sufficient time for a user to recognize that sufficient sample has been applied to the sample receiving member 12 and to cease application of the sample. When the first time period of illumination ceases, the user may thusly be informed that the test is underway. The beginning of illumination of the second time period can inform the user that the test is completed, and the test result is ready for evaluation. As noted above, the first pre-set time period may be activated by the signal from the fluid sensor. The second pre-set time period may be activated based upon passing of an estimated time for completion of a test that the diagnostic test device is configured to carry out. The time of separation between the first time period of illumination and the second time period of illumination may be about 30 seconds to about 120 seconds, about 45 seconds to about 120 seconds, about 60 seconds to about 120 seconds, or about 45 seconds to about 90 seconds.

The illumination for the second time period (e.g., indicating that the test is complete and to improve readability of the test result) may be for only a pre-set time, such as about 30 seconds to about 300 seconds, about 30 seconds to about 240 seconds, about 30 seconds to about 120 seconds, or about 60 seconds to about 120 seconds. This may provide sufficient time for the user to evaluate the test results. Alternatively, the second period of illumination may be indefinite and thus may persist until the power source runs out. In some embodiments, the test device may include an actuating switch (e.g., a power button). The actuating switch may be used to turn the device on for use. Likewise, the actuating switch may be used to turn off the light source after test results have been viewed, and the user is ready to dispose of the test device.

Illumination may be substantially steady during time periods as noted above so that the light is continually on during the noted time period and is continually off between the noted time periods. In some embodiments, illumination may be configured to provide one or more blinking or intermittent patterns. For example, the device may be configured to illuminate in a blinking fashion for one or more defined time periods. During one or more time periods, blinking may be substantially slow and steady. Slow and steady blinking may indicate, for example that the light source illuminates in an "on/off" pattern where the "on" time and the "off" times are substantially the same length (e.g., about 1 second, about 1.5 seconds, about 2 seconds, about 2.5 seconds, or about 3 seconds). The "on" and "off" times may thus be in any range of about 1 second to about 5 seconds. In other embodiments, a blinking pattern may be an accelerated blinking pattern where the "on" and "off" times are relatively shorter, such as less than 2 seconds, less than 1.5 seconds, less than 1 second, or less than 0.5 seconds in duration. In still further embodiments, the blinking pattern may be configured to change over time to, for example, substantially provide a countdown pattern. In this manner, blinking may start relatively slowly and then speed up over time to indicate progression of the test. One or more blinking patterns likewise may be interposed with one or more extended periods of the light being continually on or continually off. For example, the light may be continually on for a time period to indicate that a sufficient amount of sample has been applied, and a blinking pattern may then begin to indicate that the test is in progress. The blinking pattern may increase in speed as the test progresses until a constant illumination indicates that the test has completed. Any combination of continual "on", continual "off", and blinking patterns may be utilized in this manner.

The control component 60 can be configured to direct the overall functions of the test device and output one or more types of illumination that can be understood or interpreted by a user. If desired, a microprocessor may be utilized so long as any further hardware or software necessary to carry out the functions of the test device are included as well (e.g., RAM or ROM). Controllers and processors that are commercially available can be adapted for use according to the present disclosure. Preferably, the control component 60 includes programming (e.g., embedded software) that includes the requisite definitions of input signals and associated output signals to enable to the controller to direct the functions of the test device, as otherwise disclosed herein.

In one or more embodiments, the present disclosure further provides methods for improving ease of use of a diagnostic test device. The methods may particularly apply to improving the ease of use of a test device configured to detect the presence of an analyte in a fluid sample applied to the sample receiving member and provide an analog signal that is visible through the viewing window. Such methods can include preparing or providing a test device that is substantially as otherwise described herein. In particular, the methods can include configuring the control component of the test device to provide one or more indicia to a user that a sufficient volume of a fluid sample has been applied to the sample receiving member and automatically supply power from the power source to the light source upon passing of an estimated time for completion of a test that the diagnostic test device is configured to carry out. The visibility of the analog signal is improved by the presence of the illumination through the viewing window provided by the light source upon the passing of the estimated time for completion of the test that the diagnostic test device is configured to carry out.

The terms "about" or "substantially" as used herein can indicate that certain recited values or conditions are intended to be read as encompassing the expressly recited value or condition and also values or conditions that are relatively close thereto. For example, a value of "about" a certain number or "substantially" as certain value can indicate the specific number or value as well as numbers or values that vary therefrom (+ or −) by 5% or less, 4% or less, 3% or less, 2% or less, or 1% or less. Likewise, a statement "about" a certain condition or "substantially" a certain condition can indicate that the condition is exactly met or that the condition encompasses normal variations that would be expected to occur in manufacturing and/or that are acceptable variations that do not affect the reason or use for the stated condition. In some embodiments, the values or conditions may be defined as being express and, as such, the term "about" or "substantially" (and thus the noted variances) may be excluded from the express value.

Many modifications and other embodiments of the disclosure set forth herein will come to mind to one skilled in the art to which these disclosures pertain having the benefit of the teachings presented in the foregoing descriptions. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A diagnostic test device comprising:
   a housing having a viewing window;
   a sample receiving member extending between a proximal end positioned within the housing and a distal end extending outward from the housing;
   a test member positioned within the housing, the test member extending between a distal end in fluid communication with the proximal end of the sample receiving member and a proximal end such that a portion of the test member is visible through the viewing window;
   a fluid sensor positioned within the housing and arranged to be in communication with the sample receiving member;
   a power source positioned within the housing;
   a light source positioned within the housing, the light source configured to provide illumination that is externally visible through the viewing window; and
   a control component;

wherein the fluid sensor is in electrical connection with one or more of the power source and the control component, and the control component is configured to automatically supply power from the power source to the light source for one or more time periods after receiving a signal from the fluid sensor by the electrical connection.

2. The diagnostic test device of claim 1, wherein the test member comprises a release medium in fluid communication with a capture medium, and wherein a portion of the capture medium is visible through the viewing window.

3. The diagnostic test device of claim 1, wherein the test device is configured to detect the presence of an analyte in a fluid sample applied to the sample receiving member.

4. The diagnostic test device of claim 3, wherein the presence of the analyte is indicated by an analog signal that is visible through the viewing window.

5. The diagnostic test device of claim 3, wherein the analyte is selected from the group consisting of human chorionic gonadotropin (hCG), luteinizing hormone (LH), follicle stimulating hormone (FSH), thyroid stimulating hormone, estrogen, progesterone, testosterone, a metabolite thereof, and combinations thereof.

6. The diagnostic test device of claim 1, wherein at least the portion of the test member that is visible through the viewing window is light permeable.

7. The diagnostic test device of claim 1, wherein the fluid sensor is configured as an electrical circuit that includes the sample receiving member.

8. The diagnostic test device of claim 7, wherein the fluid sensor includes a pair of electrical contacts that are physically separated and are in contact with the sample receiving member.

9. The diagnostic test device of claim 8, wherein the pair of electrical contacts are in electrical connection with the control component.

10. The diagnostic test device of claim 1, wherein the fluid sensor is configured to signal that a fluid applied to the sample receiving member is present at a suitable volume for the test device to carry out a specified test.

11. The diagnostic test device of claim 1, wherein the light source is positioned within the housing such that the test member is between the light source and the viewing window.

12. The diagnostic test device of claim 1, wherein the light source includes a light emitting diode (LED) and a light guide.

13. The diagnostic test device of claim 12, wherein the LED is positioned so as to be off-set from the viewing window, and wherein the light guide is configured to transmit light from the LED to the viewing window.

14. The diagnostic test device of claim 13, wherein the light guide defines an illumination zone positioned within the housing such that the test member is between the illumination zone and the viewing window.

15. The diagnostic test device of claim 1, wherein the light source is further visible through a section of the housing.

16. The diagnostic test device of claim 1, wherein the control component is configured to execute one or more functions after receiving the signal from the fluid sensor, said one or more functions being effective to provide indicia to a user that a sufficient volume of a fluid sample has been applied to the sample receiving member.

17. The diagnostic test device of claim 16, wherein the one or more functions comprises supplying power from the power source to the light source for a pre-set time period.

18. The diagnostic test device of claim 1, wherein the control component includes a timer.

19. The diagnostic test device of claim 18, wherein the control component is configured to supply power from the power source to the light source for one or more pre-set time periods measured by the timer.

20. The diagnostic test device of claim 1, wherein the control component is configured to supply power from the power source to the light source for a first pre-set time period and a second pre-set time period, the first pre-set time period and the second pre-set time period being non-overlapping.

21. The diagnostic test device of claim 20, wherein the first pre-set time period is activated by the signal from the fluid sensor.

22. The diagnostic test device of claim 20, wherein the second pre-set time period is activated based upon passing of an estimated time for completion of a test that the diagnostic test device is configured to carry out.

23. The diagnostic test device of claim 1, wherein the control component is configured to supply power from the power source to the light source such that the light source provides one or more blinking effects.

* * * * *